United States Patent
Simon et al.

(10) Patent No.: US 9,981,337 B2
(45) Date of Patent: May 29, 2018

(54) DIAGNOSTIC SYSTEM AND METHOD FOR TESTING INTEGRITY OF STACK DURING ULTRASONIC WELDING

(71) Applicants: William P. Simon, New Milford, CT (US); John Massa, Waterbury, CT (US); James A. Markus, Seymour, CT (US)

(72) Inventors: William P. Simon, New Milford, CT (US); John Massa, Waterbury, CT (US); James A. Markus, Seymour, CT (US)

(73) Assignee: Sonics & Materials, Inc., Newton, CT (US)

( * ) Notice: Subject to any disclaimer, the term of this patent is extended or adjusted under 35 U.S.C. 154(b) by 199 days.

(21) Appl. No.: 14/711,115

(22) Filed: May 13, 2015

(65) Prior Publication Data
US 2015/0330952 A1     Nov. 19, 2015

Related U.S. Application Data

(60) Provisional application No. 61/992,680, filed on May 13, 2014.

(51) Int. Cl.
*G01N 29/12* (2006.01)
*B23K 20/10* (2006.01)
(Continued)

(52) U.S. Cl.
CPC ............ *B23K 20/10* (2013.01); *B06B 1/0246* (2013.01); *B06B 3/00* (2013.01); *B23K 31/125* (2013.01);
(Continued)

(58) Field of Classification Search
CPC .............. G01N 29/12; G01N 29/4418; G01N 29/4427; G01N 29/46; G01N 2291/267;
(Continued)

(56) References Cited

U.S. PATENT DOCUMENTS 3,573,781 A * 4/1971 Shoh .................. B23K 20/10
228/1.1
5,435,863 A * 7/1995 Frantz .................. B06B 1/0246
156/358

(Continued)

OTHER PUBLICATIONS

Dukane Electronics, User's Manual, Ducane Part No. 403-542-00.1, 2000-2001.*

(Continued)

*Primary Examiner* — Manish S Shah
*Assistant Examiner* — Suman K Nath
(74) *Attorney, Agent, or Firm* — Forge IP, PLLC

(57) ABSTRACT

A method for testing the integrity of a stack during ultrasonic welding, includes the steps of: (i) ultrasonically welding two or more work pieces with a stack, the stack including a convertor and a horn; (ii) measuring a frequency profile based on a vibration of the horn during the welding step; and (iii) comparing the measured frequency profile to a standard frequency profile to obtain an error rate, the error rate being indicative of a difference between the measured frequency profile and the standard frequency profile. A system employing the aforementioned method is also provided.

15 Claims, 4 Drawing Sheets

(51) Int. Cl.
*G01N 29/34* (2006.01)
*B29C 65/82* (2006.01)
*B06B 3/00* (2006.01)
*B23K 31/12* (2006.01)
*G01N 29/44* (2006.01)
*B06B 1/02* (2006.01)
*B29C 65/08* (2006.01)
*B29C 65/00* (2006.01)
*B23K 101/32* (2006.01)
*B23K 101/38* (2006.01)

(52) U.S. Cl.
CPC ......... *B29C 65/8292* (2013.01); *G01N 29/12* (2013.01); *G01N 29/348* (2013.01); *G01N 29/4427* (2013.01); *B06B 2201/40* (2013.01); *B06B 2201/72* (2013.01); *B23K 2201/32* (2013.01); *B23K 2201/38* (2013.01); *B29C 65/08* (2013.01); *B29C 66/1122* (2013.01); *B29C 66/43* (2013.01); *B29C 66/8322* (2013.01); *B29C 66/96* (2013.01); *G01N 2291/267* (2013.01)

(58) Field of Classification Search
CPC .............. B06B 1/0246; B06B 2201/40; B06B 2201/72; B29C 65/8292; B29C 66/96
USPC ............ 73/588, 602, 648; 156/580.1, 580.2; 228/1.1, 110.1
See application file for complete search history.

(56) References Cited

U.S. PATENT DOCUMENTS

| | | | |
|---|---|---|---|
| 8,016,964 B2 | 9/2011 | Simon et al. | |
| 8,113,258 B2 | 2/2012 | Patrikios et al. | |
| 8,627,996 B2 | 1/2014 | Patrikios | |
| 9,144,937 B2 * | 9/2015 | Klinstein | B29C 66/961 |
| 2011/0146408 A1 * | 6/2011 | Aoyagi | B23K 20/007 73/588 |
| 2011/0220292 A1 * | 9/2011 | Short | B23K 20/103 156/580.1 |
| 2013/0284379 A1 | 10/2013 | Patrikios et al. | |

OTHER PUBLICATIONS

Branson Ultrasonic Corporation, ISO Certification, TL-3 manual, 1999.*

* cited by examiner

… (1) …

DIAGNOSTIC SYSTEM AND METHOD FOR TESTING INTEGRITY OF STACK DURING ULTRASONIC WELDING

FIELD OF THE INVENTION

The present invention relates to ultrasonic welding systems and methods of using the same. More specifically, the present invention relates to a method and system for testing the integrity of a stack of an ultrasonic welding system.

BACKGROUND OF THE INVENTION

Ultrasonic welding uses high frequency vibrations to weld two or more work pieces. This process has applications in the electronic, automotive, aerospace, appliance, and medical industries, for example, and is commonly used for metals and plastics.

The process of ultrasonic welding and the equipment and systems to perform the same are generally known. In reference to FIG. 1, a generic ultrasonic welding system 10 is shown. The system 10 shown in FIG. 1 is configured to weld two wires 22, 24 using ultrasonic vibrations. The system 10 includes an anvil 20. An end of a first wire 22 and an end of a second wire 24 are positioned in an overlapping manner on a surface of the anvil 20. The system 10 includes a stack 30 for transferring energy in the form of ultrasonic vibrations to the ends of the two wires 22, 24 to form the weld. The stack 30 includes a converter 32 for converting electric power into mechanical vibrations, a booster 34 for optionally modifying the amplitude of the vibrations generated by the convertor 32, and a horn 36 for applying the vibrations to the ends of the wires 22, 24. A power supply 40 delivers a high power AC signal to the convertor 32. A controller 50 controls and monitors the system 10.

During operation of the ultrasonic welding system 10, a force is applied to the stack 30, thereby compressing the ends of the two wires 22, 24 between the horn 36 and the anvil 20. The power supply 40 is actuated via the controller 50 to provide power to the convertor 32, creating a high frequency vibration. The vibration is transmitted through the booster 34, which may amplify the vibration. The vibration is then transmitted to the horn 36 which applies it to the ends of the two wires 22, 24 thereby welding them together.

A disadvantage of such systems is that if insufficient energy is transmitted to the parts being welded via the vibrations of the horn, it can result in an inferior weld that does not meet established criteria for a desired application.

Another disadvantage of such systems is that any defect with the power supply or the stack can result in insufficient energy being used to form the weld, resulting in a substandard weld. In some cases, the poor quality of the weld is evident upon inspection and the part is discarded. Nevertheless, if a substandard weld is discovered, an inspection of the welding system should be performed to determine the reason for the substandard weld.

A disadvantage with diagnosing such systems is that it is difficult to determine whether the substandard weld is a result of a problem with the power supply, the stack, or both. This disadvantage can result in significant, and costly, downtime to diagnose and correct the problem. The stack is typically a complex and precise instrument and, therefore, it is time consuming and difficult to identify and correct errors associated therewith. As a result, there is a tendency to attribute poor quality welds to errors with the power source instead of the stack, even when the power source is operating according the specification. This can result in incurring unnecessary costs to repair or replace the power source.

Another disadvantage of such ultrasonic welding systems is that in some cases, a problem with the stack results in a substandard weld, albeit one that is not perceptible to operator of the system. In such circumstances, the substandard weld may be discovered in a subsequent quality control check. In such cases, an entire lot of welded work pieces may be discarded. In other circumstances, the substandard weld may not be identified.

It is an object of the present invention to overcome these disadvantages and other disadvantages associated with the prior art.

SUMMARY OF THE INVENTION

In accordance with one aspect of the invention, a method for testing the integrity of a stack during ultrasonic welding, includes the steps of: (i) ultrasonically welding two or more work pieces with a stack, the stack including a convertor and a horn; (ii) measuring a frequency profile based on a vibration of the horn during the welding step; and (iii) comparing the measured frequency profile to a standard frequency profile to obtain an error rate, the error rate being indicative of a difference between the measured frequency profile and the standard frequency profile.

In some embodiments, the method further includes the step of providing an error indication to the extent the obtained error rate is greater that a threshold error rate.

In some embodiments, the measured frequency profile comprises a frequency associated with the horn at a first time $T_1$. In some embodiments, the measured frequency profile comprises a measured frequency associated with the horn that varies over a period of time $(T_1-T_2)$.

In some embodiments, at least a portion of the measured frequency profile is disregarded during the comparing step in order to reduce potential effects of anomalies. In certain embodiments, the measured frequency profile is generated for a time that is less than an entire duration of the welding step.

In some embodiments, the measured frequency profile comprises a graph of frequency versus time. In certain of these embodiments, the standard frequency profile comprises a graph of frequency versus time.

In accordance with another aspect of the present invention, a system for testing the integrity of a stack during ultrasonic welding, includes a controller having a processor and software executing thereon, a power source in communication with the controller, and a stack in communication with the power source and with the controller. Software executing on the controller receives a signal indicative of a frequency profile of the stack, and software executing on the controller compares the received frequency profile with a standard frequency profile to obtain an error rate.

DETAILED DESCRIPTION OF THE INVENTION

The inventors have discovered new methods and systems that overcome many of the problems associated with the prior art. Specifically, the inventors have discovered a method and system for testing the integrity of a stack during ultrasonic welding by comparing a measured frequency profile of the stack during an ultrasonic weld with a standard frequency profile for the stack.

Figure 2:
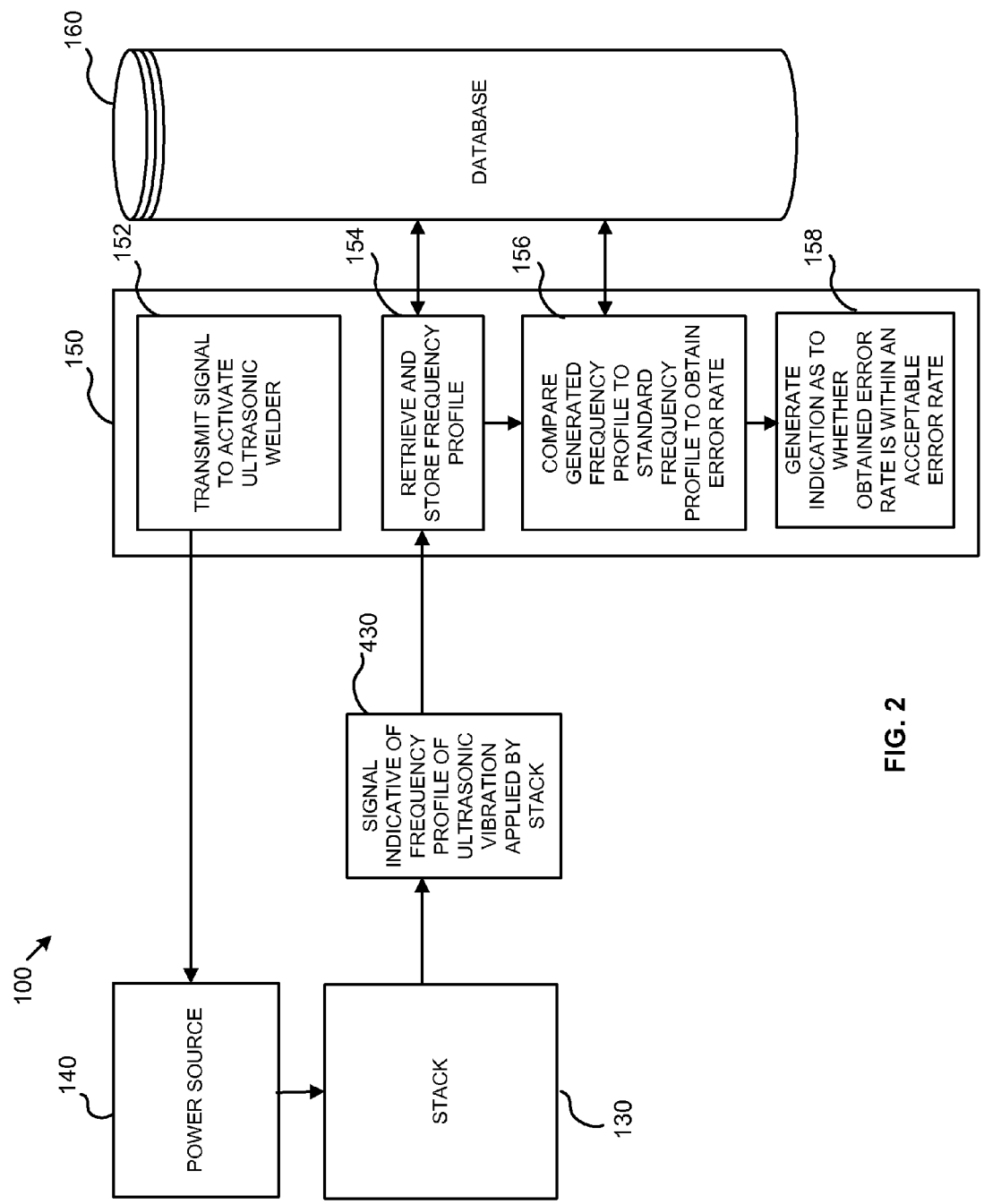
FIG. 2 is a diagnostic system in accordance with one embodiment of the present invention for testing the integrity of a stack during ultrasonic welding.

In reference to FIG. 2, a system 100 in accordance with one embodiment of the present is shown. The system 100 includes a controller 150. The controller 150 may be, for example, a standard processor based computer system having software executing thereon and a data storage associated therewith. Such generic controllers are known in the art, for example, the "WSC Controller" manufactured by Sonics & Materials, Inc. of Newtown, Conn. The "WSC Controller" includes a power source integrated therein, however, a person of ordinary skill in the art will understand that the power source and the controller may be separate, for example, as illustrated in the embodiment shown in FIG. 2.

Figure 1:
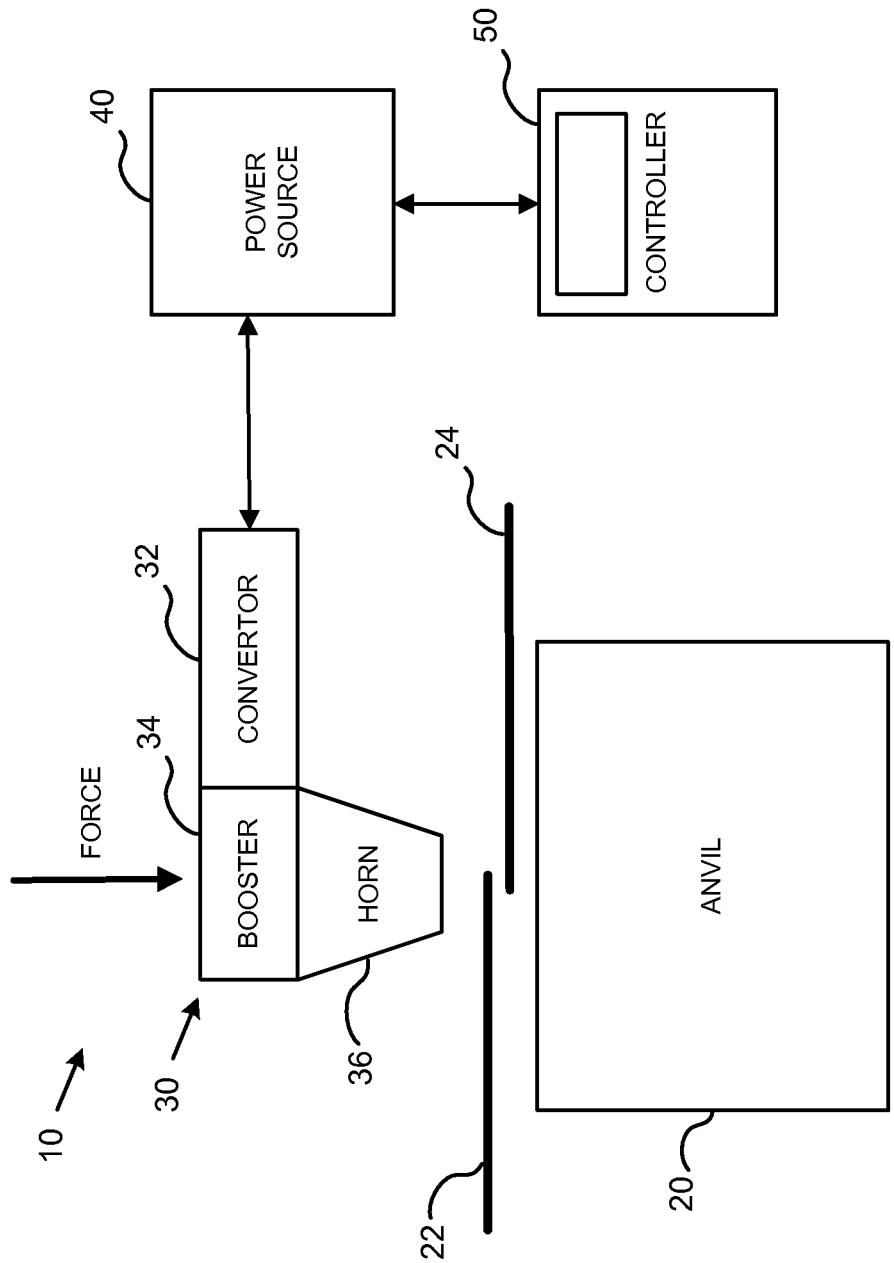
FIG. 1 illustrates an ultrasonic welding system in accordance with the prior art.

The controller 150 is in communication with a power source 140. The power source 140 is in electric communication with a stack 130. The power source 140 is configured to transmit electric energy to the stack 130. The stack 130 is similar to the stack 30 shown in FIG. 1. The stack 130 draws electric energy from the power source 140 and converts it to mechanical energy in the form of ultrasonic vibrations. The stack 130 includes a converter for converting electric energy from the power source 140 into mechanical vibrations, a booster for modifying the amplitude of the vibrations generated by the convertor, and a horn for applying the vibrations to the parts being welded. The stack 130 is in communication with the controller 150 and is configured to generate and transmit a signal indicative of the actual, also referred to a measured or generated, frequency profile representing the ultrasonic vibration applied to the work pieces being welded.

Figure 3A:
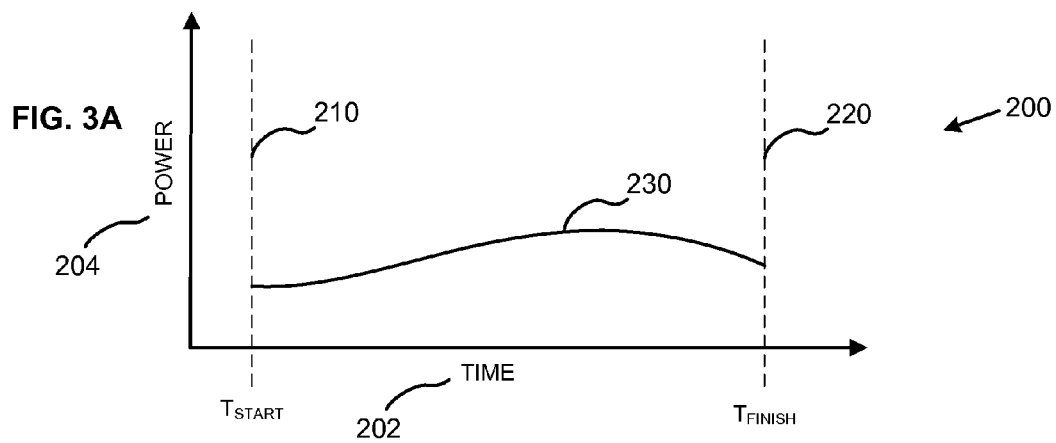
FIG. 3A illustrates a power profile representing the power drawn from the power source by the convertor during an ultrasonic weld.

During operation of the system 100, software 152 executing on the controller 150 transmits a signal to the power source to activate the ultrasonic welder. In reference to FIG. 3A, a chart 200 illustrating a power profile 230 is shown. Time is represented on the x-axis 202 of the chart 200 and power is represented on the Y-axis 204 of the chart. In the embodiment shown, the power profile 230 represents power drawn by the stack during a period of time from $T_{START}$ 210 to $T_{FINISH}$ 220. It should be understood that the power profile 230 shown in FIG. 3A is intended to aid in understanding the present invention, and is not intended to limit the disclosure in any way. Such a power profile may take on many different configurations and shapes, based upon different variables, including the type of power source and the type of stack.

The convertor associated with the stack 130 (not shown in FIG. 2) converts the electric energy from the power source 140 to mechanical energy in the form of ultrasonic vibrations. The mechanical energy is then transmitted through the stack 130 via an optional booster and then to the horn. The work pieces are compressed between the anvil and the horn. The horn vibrates at the ultrasonic frequency, applying energy to the work pieces and creating the weld. The stack 130 is configured to generate a signal indicative of the frequency profile 430 of the stack 130 (discussed below). The stack 130 is in communication with the controller 150 and transmits the signal indicative of the frequency profile 430 to the controller 150.

Software 154 executing the controller 150 receives the frequency profile 430 from the stack 130 and optionally stores the frequency profile in the database 160. Software 156 executing on the controller 150 obtains a standard frequency profile 330 from the database 160 and compares it to the measured frequency profile 430 generated by the stack 130 to determine whether the stack is properly generating vibrations in response within a predetermined margin of error.

Figure 3B:
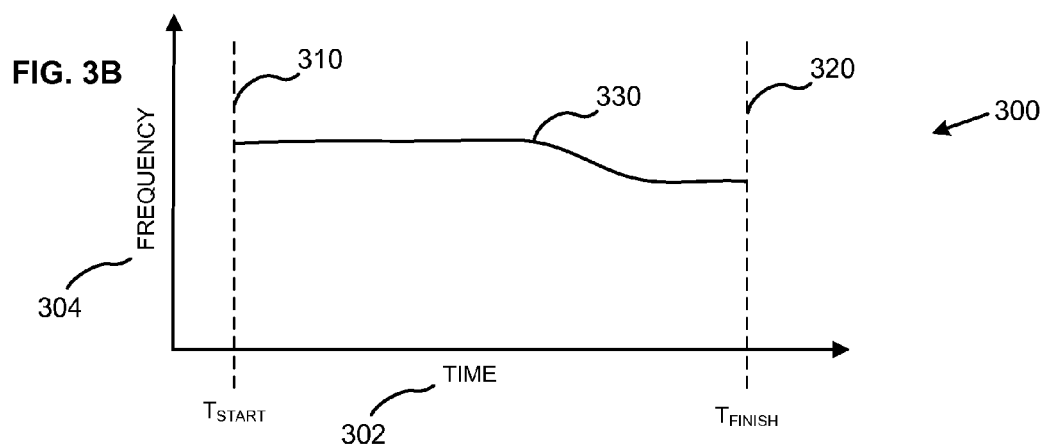
FIG. 3B illustrates a standard frequency profile of a stack during an ultrasonic weld.

In reference to FIG. 3B, a chart 300 illustrating a standard frequency profile 330 is shown. Time is represented on the x-axis 302 of the chart 300 and frequency is represented on the Y-axis 304 of the chart 300. In the embodiment shown, the standard frequency profile 330 represents a frequency profile that the specified stack 130 is intended to generate under normal operating conditions. The standard frequency profile 330 may be generated from data collected during prior runs of the ultrasonic welding machine, or may be supplied by a vendor of the machine, or a third party.

Figure 3C:
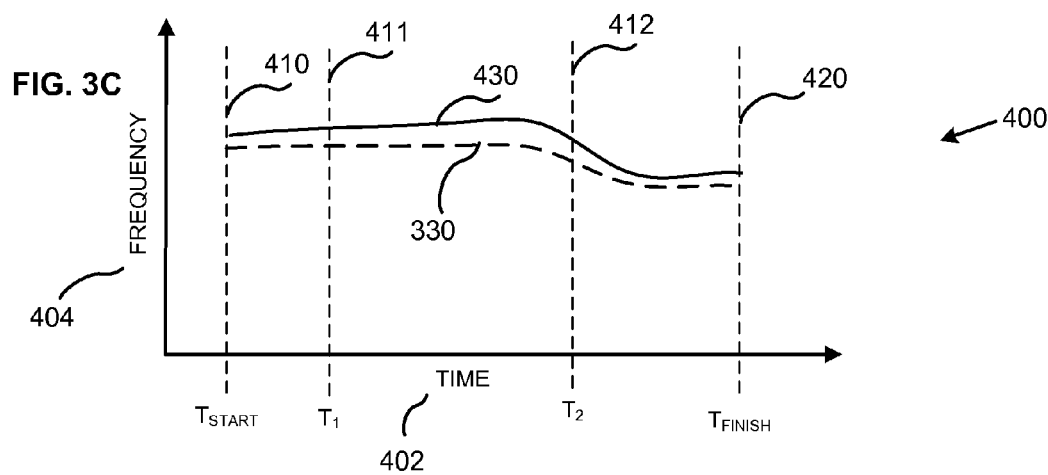
FIG. 3C illustrates a comparison between a measured frequency profile and a standard frequency profile.

Software 156 executing on the controller 150 compares the measured frequency profile 430 corresponding with the standard frequency profile 330 and determines a rate of error between the two. This comparison step is illustrated in FIG. 3C, wherein the standard frequency profile 330 is illustrated with a dashed line and the measured frequency profile 430 is illustrated with a sold line. Time is represented on the x-axis 402 of the chart 400 and frequency is represented on the Y-axis 404 of the chart 400. The chart 400 illustrates frequencies between a start time 410 and a finish time 420.

In reference to FIG. 3C there is a perceptible difference between the standard frequency profile 330 and the measured frequency profile 430. The software 156 executing on the controller determines an error rate for one or more times during the power profile 230. For example, at $T_1$ 411 the software 156 compares the frequency of the standard frequency profile 330 at $T_1$ to the measured frequency profile 430 at $T_1$ to determine a rate of error at $T_1$. Depending on system 100, the software 156 may calculate a plurality of different error rates at different times, for example $T_2$ to $T_{N+2}$ during the power profile.

The software 156 compares the generated error rates to an acceptable error rate that is stored in the system 100. If a predetermined number of the generated error rates exceed the acceptable error rate, software 158 executing on the controller 150 generates an indication that the generated error rates is outside of the predetermined acceptable error rate, indicating a problem with the stack 130. If a predetermined number of the generated error rates do not exceed the acceptable error rate, software 158 executing on the controller 158 generates an indication that the obtained error rates is within the acceptable error rate, indicating that the stack 130 is working correctly.

If the obtained error rates are within the acceptable error rate, this indicates that the stack 130 is working correctly. If however, the obtained error rates are outside of the acceptable error rate, this indicates that there is a problem with stack 130 that needs to be addressed, and that the problem is not related to the power source 140. In some embodiments of the present invention, the system is configured to provide a visual indicator of whether or not each stack use is acceptable.

It should be understood to a person of ordinary skill in the art that the magnitude of the error rates may vary depending on any number of factors. Similarly, software executing on the system may configured to ignore errors at certain times during the profile, to the extent that the majority of the times during the profile do not exceed the acceptable error. This configuration allows for certain anomalies inherent in any welding system that would not substantially affect the quality of the weld.

In some embodiments of the present invention, the hardware for welding and collecting such frequency data is already employed in the field. In such systems it is possible to obtain a software upgrade, which could include a data set corresponding to standard frequency profiles that would enable the present invention to be practiced on the existing system.

Figure 4:
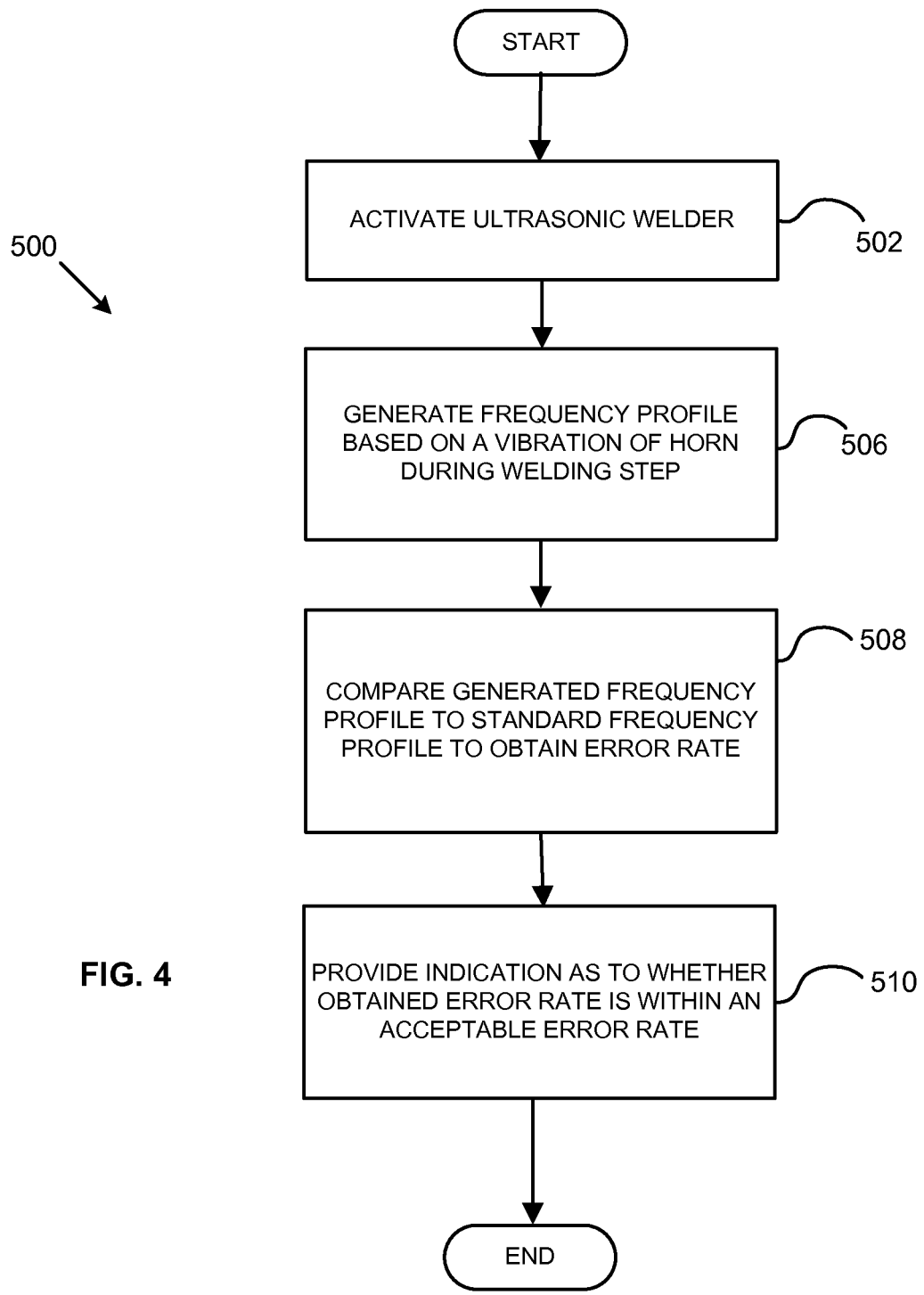
FIG. 4 illustrates a method in accordance with one embodiment of the present invention.

In reference to FIG. 4, a flow chart 500 illustrating a method in accordance with one embodiment of the present invention is illustrated. The method 500 includes the step 502 of transmitting from the controller to activate the ultrasonic welder. Next, the method 500 includes the step 506 of generating a frequency profile based on a vibration of a horn during the welding. Next, the method 500 includes the step 508 of comparing the generated frequency profile to a standard frequency profile to obtain an error rate. Next, the method 500 includes the step 510 of providing in indication as to whether the obtained error rate is within an acceptable error rate.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A method for testing the integrity of a stack during ultrasonic welding, comprising the steps of:
    ultrasonically welding two or more work pieces with a stack,
    measuring a frequency profile during the welding step;
      wherein the measured frequency profile comprises a frequency associated with the stack over a period of time (T1-T2);
    comparing the measured frequency profile to a standard frequency profile to obtain an error rate, wherein the error rate being indicative of a difference between the measured frequency profile and the standard frequency profile over the period of time; and
    determining a problem with the integrity of the stack to the extent that the obtained error rate is greater than a threshold error rate.

2. The method of claim 1, further comprising the step of: providing an error indication to the extent that the obtained error rate is greater than a threshold error rate.

3. The method of claim 1, wherein at least a portion of the measured frequency profile is disregarded during the comparing step in order to reduce potential effects of anomalies.

4. The method of claim 1, wherein the measured frequency profile is generated for a time that is less than an entire duration of the welding step.

5. The method of claim 1, wherein the measured frequency profile comprises a graph of frequency versus time.

6. The method of claim 5, wherein the standard frequency profile comprises a graph of frequency versus time.

7. A system for testing the integrity of a stack during ultrasonic welding, comprising:
    a controller having a processor;
    a power source in communication with the controller;
    a stack in communication with the power source and with the controller; and
    a software executing on the processor of the controller for receiving a frequency profile of the stack for comparing the received frequency profile with a standard frequency profile to obtain an error rate and for determining is a problem with the integrity of the stack to the extent that the obtained error rate is greater than a threshold error rate;
      wherein the measured frequency profile comprises a frequency associated with the stack over a period of time (T1-T2); and the error rate being indicative of a difference between the measured frequency profile and the standard frequency profile over the certain period of time.

8. The system of claim 7 further comprising: the software executing on the controller for providing an error indication to the extent that the obtained error rate is greater that a threshold error rate.

9. The system of claim 7, wherein at least a portion of the measured frequency profile is disregarded during the comparing step in order to reduce potential effects of anomalies.

10. The system of claim 7, wherein the measured frequency profile is generated for a time that is less than an entire duration of the welding step.

11. The system of claim 7, wherein the measured frequency profile comprises a graph of frequency versus time.

12. The system of claim 11, wherein the standard frequency profile comprises a graph of frequency versus time.

13. A system for testing the integrity of a stack during ultrasonic welding, comprising:
    a controller having a processor;
    a power source in communication with the controller;
    a stack in communication with the power source and with the controller; and
    software executing on the controller for receiving a signal indicative of a frequency profile of the stack;
    a software executing on the processor of the controller for receiving a frequency profile of the stack, for comparing the received frequency profile with a standard frequency profile to obtain an error rate, for determining a problem with the integrity of the stack to the extent that the obtained error rate is greater than a threshold error rate, and for providing an error indication to the extent that the obtained error rate is greater than the threshold error rate; and
    wherein the measured frequency profile and the standard frequency profile each comprises a graph of frequency versus time and the measured frequency profile comprises a frequency associated with the stack over a period of time (T1-T2).

14. The system of claim 13, wherein at least a portion of the measured frequency profile is disregarded during the comparing step in order to reduce potential effects of anomalies.

15. The system of claim 13, the measured frequency profile is generated for a time that is less than an entire duration of the welding step.

* * * * *